United States Patent
Könst et al.

(10) Patent No.: US 11,098,020 B2
(45) Date of Patent: Aug. 24, 2021

(54) BIOMASS CONVERSION

(71) Applicant: Nederlandse Organisatie voor toegepast-natuurwetenschappelijk onderzoek TNO, 's-Gravenhage (NL)

(72) Inventors: Paul Mathijs Könst, 's-Gravenhage (NL); Johan Urbanus, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 0 days.

(21) Appl. No.: 16/304,087

(22) PCT Filed: May 23, 2017

(86) PCT No.: PCT/NL2017/050328
§ 371 (c)(1),
(2) Date: Nov. 21, 2018

(87) PCT Pub. No.: WO2017/204634
PCT Pub. Date: Nov. 30, 2017

(65) Prior Publication Data
US 2019/0263766 A1 Aug. 29, 2019

(30) Foreign Application Priority Data
May 23, 2016 (EP) .................... 16170916

(51) Int. Cl.
- *C07D 307/50* (2006.01)
- *B01D 11/04* (2006.01)
- *B01J 19/18* (2006.01)
- *C07D 307/38* (2006.01)

(52) U.S. Cl.
CPC ........ *C07D 307/50* (2013.01); *B01D 11/0492* (2013.01); *B01J 19/1868* (2013.01); *C07D 307/38* (2013.01); *B01J 2219/00033* (2013.01)

(58) Field of Classification Search
CPC .................................................. C07D 307/50
See application file for complete search history.

(56) References Cited

U.S. PATENT DOCUMENTS

| 7,572,925 B2 | 8/2009 | Dumesic et al. |
| 2008/0033188 A1 | 2/2008 | Dumesic et al. |
| 2012/0302765 A1 | 11/2012 | Dumesic et al. |
| 2012/0302767 A1* | 11/2012 | Dumesic .............. C07D 307/50 549/326 |
| 2013/0150595 A1 | 6/2013 | Dumesic et al. |
| 2014/0107355 A1 | 4/2014 | Dumesic et al. |

FOREIGN PATENT DOCUMENTS

| WO | WO-2011/071386 | 6/2011 |
| WO | WO-2012/115706 | 8/2012 |

OTHER PUBLICATIONS

Gourdon, Pr. Christophe. "Pulsing Operation of Multiphase Reactors." PI Expert Meeting (Sep. 10, 2014. (Year: 2014).*
International Search Report and Written Opinion for PCT/NL2017/050328, dated Jul. 25, 2017, 8 pages.
Higson et al., "Chemical cascades in water for the synthesis of functionalized aromatics from furfurals," Green Chem. (2016) 18:1855.
Rivalier et al., "Development of a continuous catalytic heterogeneous column reactor with simultaneous extraction of an intermediate product by an organic solvent circulating in countercurrent manner with the aqueous phase," Catalysis Today (1995) 24:165-171.
Van Putten et al., "Hydroxymethylfurfural, a versatile platform chemical made from renewable resources," Chem. Rev. (2013) 113:1499-1597.

* cited by examiner

*Primary Examiner* — John S Kenyon
(74) *Attorney, Agent, or Firm* — Banner & Witcoff, Ltd.

(57) ABSTRACT

Processes and reactor systems for biomass conversion are described. A continuous process for the conversion of carbohydrate-containing feed material into furanic compounds comprises a reaction step comprising subjecting said feed material to reaction conditions in a reaction medium comprising two immiscible liquid phases, including a reactive phase and an extractive phase, and a Brønsted acid as catalyst, wherein the reaction medium comprises a solid component comprising at least a part of a carbohydrate-containing fraction of said feed material.

15 Claims, 4 Drawing Sheets

BIOMASS CONVERSION

CROSS-REFERENCE TO RELATED APPLICATIONS

This application is the national phase of PCT application PCT/NL2017/050328 having an international filing date of 23 May 2017, which claims benefit of European patent application No. 16170916.7 filed 23 May 2016. The contents of the above patent applications are incorporated by reference herein in their entirety.

The present invention generally relates to the conversion of biomass, in particular to conversion of carbohydrate-containing solid material into furanic compounds.

The production of chemical compounds from renewable sources, especially from biomass and waste streams, is desired in order to reduce the dependency on fossil oil and to reduce the $CO_2$ footprint of such compounds, further in view of growing demand and diminishing oil reserves. Furanic compounds have been identified as key platform chemicals for the production of compounds from biomass, including biomass derived aromatic compounds. Although several technologies are under development, there is a need for more flexible, energy efficient and large scale processes. A particular focus of research is the development of processes for the production of 5-(hydroxymethyl)-2-furaldehyde (HMF) from biomass. An important aim is reducing the hydrolysis of formed HMF to products such as levulinic acid. The use of a biphasic reaction medium has been proposed in order to provide for extraction of formed HMF, thereby reducing at least the undesirable hydrolysis of HMF to levulinic acid. A background reference for such processes is given in Van Putten et al., *Chem. Rev.* 113 (2013), 1499-1597. Further background references include US 2008/0033188; U.S. Pat. No. 7,572,925; US 2012/0302765; US 2012/0302767; US 2013/0150595; US 2014/0107355; and WO 2012/115706. These references generally do not exemplify continuous processes, in particular not processes that are adapted for heterogeneous feed streams. Rivalier et al., *Catalysis Today,* 24 165-171 (1995) describes a continuous heterogeneous column reactor for the dehydration of hexoses into HMF, using a zeolite as acid catalyst in suspension in aqueous phase, and with cut discs packing and with the lower settler connected to a pneumatic pulsator.

Furthermore Higson et al. *Green Chem.* 2016, 18, 1855, mentions that furfural dimethylhydrazone prepared from furfural was reacted with maleic anhydride or N-ethyl maleimide in chloroform to give aromatic products.

Yet a further desire is to develop processes that utilize one or more waste stream to produce furanic compounds. Particularly desirable are processes that can use waste streams comprising cellulose. An object of the present invention is therefore to provide a process for the conversion of biomass into furanic compounds that address one or more of the above-mentioned desires at least in part. A further object is to provide processes which are continuous processes and/or processes that are suitable for heterogeneous feed streams.

In order to better address one or more of the above mentioned desires at least in part, a process is provided for the conversion of carbohydrate-containing feed material, wherein the process comprises subjecting such feed material to reaction conditions in a multiphasic reaction medium and/or wherein a pre-treatment and/or post-treatment is used.

In an aspect, the invention pertains to a continuous process for the conversion of carbohydrate-containing feed material into furanic compounds, the process comprising a reaction step comprising subjecting said feed material to reaction conditions in a reaction medium comprising two immiscible liquid phases, including a reactive phase and an extractive phase, and a Brønsted acid as catalyst, wherein the reaction medium comprises a solid component comprising at least a part of a carbohydrate-containing fraction of said feed material.

The invention also pertains to a reactor system for the conversion of biomass to furanic compounds, comprising:
optionally a pre-treatment section,
a reactor comprising an inlet and an outlet wherein the reactor is configured for continuous operation and for transport of components of a reaction medium from an inlet to an outlet,
preferably a pulsating device in fluid communication with said reactor for providing reciprocating flow to a reaction medium in said reactor,
one or more separation units downstream of said reactor for solid/liquid separation and for liquid/liquid separation of a reactive phase from an extractive phase of the reaction medium,
a recovery unit for recovering product from the separated extractive phase, and a recycling loop from said recovery unit to said reactor for recycling of the extractive phase, and preferably a recycle loop for said reactive phase to said reactor,
optionally a downstream processing unit in fluid connection with said reactor for subjecting formed furanic compounds to chemical reactions.

BRIEF DESCRIPTION OF THE DRAWINGS

The foregoing and other features and advantages of the present invention will be more fully understood from the following detailed description of illustrative embodiments taken in conjunction with the accompanying drawings in which.

Figure 1:
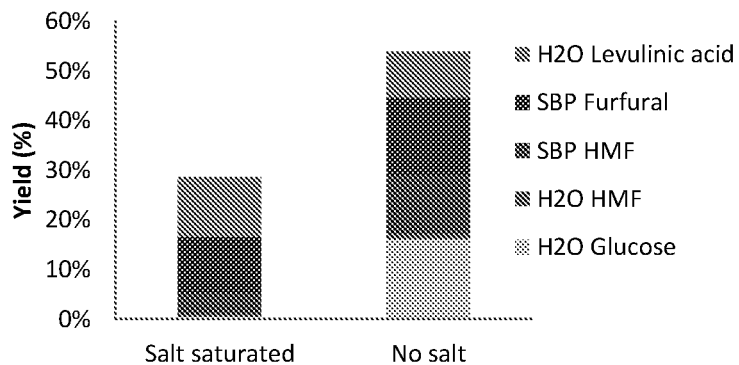
FIG. 1 is a graph showing the results of HMF yield obtained for conversion of a sewage sieve fraction as feed material in a biphasic system.

The recited "reaction conditions" are conditions (especially the temperature) effective to cause the conversion of carbohydrate-containing feed material into furanic compounds. Accordingly, alternatively and/or in addition the process comprises a reaction step comprising conversion of at least part of the feed material into furanic compounds, wherein said reaction step is carried out in the reaction medium.

Two liquid phases can be considered as "immiscible liquid phases" if the liquid phases form when mixed separate phases with an interface at the temperatures and pressures used in the reaction step, e.g. during the reaction step of the process. Hence, the reaction medium comprises a reactive liquid phase and an extractive liquid phase, wherein said liquid phases are immiscible with each other. The two phases can alternatively and/or in addition be identified as aqueous and (apolar) organic phase, or as first liquid phase comprising at least 50 wt. % water and as second liquid phase comprising at least at least 50 wt. % (apolar) organic liquid compounds, based on the liquid components of said phases.

As used herein, the term "biomass" includes but is not restricted to material containing polysaccharides, for example cellulose-containing material.

The term "Brønsted acid" refers to a Brønsted-Lowry acid and includes any chemical species that can donate or transfer one or more protons to another chemical species, and includes for example ions, molecules and solid acids. The term includes mineral acids, for example inorganic acids, such as HCl, $HNO_3$, $H_3PO_4$, and $H_2SO_4$. Solid acids include for example zeolites and acid ion-exchanged resins.

The process usually comprises one or more pre-treatment steps of said feed material upstream of or prior to said reaction step. The continuous process is hence preferably carried out in a system comprising a reactor and a pre-treatment section comprising one or more pre-treatment units upstream of said reactor, wherein the system preferably further comprises a downstream section comprising one or more downstream units downstream of said reactor. Herein, upstream and downstream refer to the flow of feed and product. The pre-treatment section preferably comprises a plurality of pre-treatment units arranged in series. Feed material is supplied to a pre-treatment unit, for example in a continuous manner as dry or wet solid material, using e.g. a screw feeder or a funnel. A feed stream may for example also be supplied as slurry. In both cases, the pre-treatment may comprise adding a liquid component to the feed and/or removing a liquid component from the feed. Preferably, the pre-treatment comprises adding or removing water from the feed, for instance by evaporation or filtration, to obtain a desired water content. In this way, the viscosity and solids content of the feed can be adjusted.

In some embodiments, the feed is solid material, which may for example be particulate material, fibrous material, granular material, and/or bulk material.

The pre-treatment optionally comprises reducing the size of particles or pieces of the feed material. Such size reduction may for instance comprise mechanical size reduction, such as by grinding, milling, and/or chopping, or for instance using rotary size reduction equipment, such as a knife mill, a hammer mill, or a disc mill. Size reduction is in particular advantageous for plant matter as feed material.

The pre-treatment may also comprise a step of steam explosion of biomass, wherein lignocellulosic biomass is exposed to steam under high pressure (e.g. at least 10 bar) and high temperature (e.g. at least 150° C.) and is rapidly depressurized (e.g. to less than 5 bar in less than 10 seconds, such as by at least 10 bar in less than 0.1 s) to cause expansion. In such case, the pH of the reaction medium can for example be in the range of 1.5 to 2.5, such as about 2.0.

The method may also comprise as pre-treatment exposure to steam, such as superheated steam. This involves for instance the continuous supply and withdrawal of steam from a unit or reactor zone having inlets and outlets for steam and comprising biomass, for example as described in WO 2011/071386. In some embodiments, the pre-treatment comprises treatment with an aqueous acid or base solution and subsequently exposure to steam, preferably steam with a pressure of between 4-8 bara and having a temperature of 150-220° C.

The pre-treatment may further comprise for example disintegrating densified biomass, such as biomass pellets. Examples of such a step include ripping, tearing and crushing, optionally upstream of a particle size reduction step.

One or more pre-treatments steps may be carried out as batch process in a batch pre-treatment unit, which can be connected with a continuous reactor for instance through a buffering unit. For instance, steps on dry biomass could be carried out as batch process steps, whereas steps after addition of liquid could be carried out as continuous process steps.

The pre-treatment may also comprises adding one or more compounds to the feed material, such as catalysts. Optionally, acid catalyst is added, for example all or part of the acid used to reach a desired pH of the reaction medium in the reactor. For example, make up acid may be added. Optionally, one or more catalysts for reactions carried out in a downstream section downstream of the reactor are already added during the pre-treatment upstream of the reactor.

The pre-treatment steps may provide for balancing of heterogeneities of the feed materials. The pre-treatment may for example comprise mixing two or more feed materials, such as two or more different solid heterogeneous feed materials or a solid and a liquid feed material. This may for instance be used to balance variations in such heterogeneous feed material. Mixing feed materials may also provide properties different from the individual components, such as pH, structure, and composition. Mixing feed materials may also allow for higher production capacities.

In a particular embodiment, the process comprises changing of feed material and/or changing one or more process parameters of the pre-treatment, preferably while the reactor continues to operate. This allows for benefitting from the robust design of the preferred continuous reactor and continuous process of the invention. Hence, in preferred embodiments, the process is advantageously suitable for a variety of feed materials. For instance, a new batch of feed material having a different composition may be applied during the process.

Generally, a stream comprising a liquid phase and carbohydrate-containing solid material is obtained from the pre-treatment section and supplied into the reactor, generally in a continuous manner. In this way, the reaction medium comprises a solid component comprising at least a part of a carbohydrate-containing fraction of said feed material. The feed material as supplied into the reactor is referred to as pre-treated feed. The pre-treated feed preferably comprises particles comprising polysaccharides.

Preferably, the solid component in the pre-treated feed and/or reaction medium comprises pieces with a size of 5 mm to 20 cm, or 1 cm to 10 cm, or 5 mm to 5 cm and/or particles with a size of less than 5 mm or less than 1 mm, usually more than 10 µm or more than 50 µm or more than 100 µm. Sizes can be measured for example with sieve analysis or with laser diffraction (Malvern Mastersizer). Preferably, the pre-treated feed comprises at least 5 wt. % or at least 10 wt. % or at least 50 wt. % of such solid component, based on dry weight of the pre-treated feed.

The process uses a carbohydrate-containing feed material. The feed material generally contains a carbohydrate-containing solid component, but the invention is not restricted to such feed materials. In a preferred embodiment, the feed material comprises biomass material, for example at least 50 wt. % or at least 90 wt. % biomass based on total dry weight of the feed material. In a preferred embodiment, the feed material is a waste material, preferably biomass-containing waste. Preferably, the feed material comprises polysaccharides, more preferably polymers comprising or consisting of $C_5$ and/or $C_6$ monosaccharide units. Usually, polysaccharides are polymeric carbohydrate molecules composed of monosaccharide units bound together by glyosidic linkages. The polysaccharides are hydrolysable to give monosaccharides. Preferably, the feed comprises as polysaccharide one or more selected from the group consisting of cellulose, hemicellulose, pectin, inulin, chitin, and starch. Preferably, the material comprises cellulose, hemicellulose and/or lignin. More preferably, the feed material comprises cellulose fibre. Optionally, the cellulose fibre comprises natural cellulose fibres comprising cellulose, hemicellulose and lignin. Optionally, the cellulose fibre comprises processed cellulose fibres comprising or essentially consisting of cellulose.

The feed material optionally comprises other biomass components, for example oils, fats, and proteins. In some embodiments, the feed material comprises non-biomass solid material, for instance at least 5 wt. % or at least 10 wt. % based on dry weight. Preferably, the feed material comprises at least 10 wt. %, or at least 20 wt. %, or at least 50 wt. %, for example 10-99 wt. %, or 25-95 wt. %, of polysaccharide, more preferably of cellulose, based on dry weight. Preferably, the feed material comprises at least 1 wt. %, more preferably at least 5 wt. % or at least 20 wt. % of cellulose and/or hemicellulose based on dry weight. In some embodiments, the feed material contains less than 90 wt. % of polysaccharides, or less than 75 wt. %, based on dry weight of the total material. Preferably, the feed material comprises at least 5 wt. %, more preferably at least 10 wt. % of hexose residues contained in polysaccharides, based on dry weight of the feed. Preferably, the feed material comprises at least 1 wt. %, or at least 5 wt. %, or at least 10 wt. % pentose residues contained in polysaccharides, based on dry weight of the feed, especially in combination with such amounts of hexose residues. Optionally, the feed material comprises at least 1 wt. % or at least 5 wt. % hemicellulose, based on dry weight. In this way, the obtained furanic compounds may comprise a mixture of furfural and HMF. These preferred amounts and compositions apply in particular also to the pre-treated feed provided into a reactor.

The process comprises subjecting the feed material, preferably after pre-treatment, to reaction conditions. The reaction conditions provide for the conversion of carbohydrate, in particular polysaccharides, into furanic compounds. This conversion generally involves hydrolysis of a polysaccharide to yield at least glucose and/or fructose and dehydration of glucose and/or fructose into a furanic compound, in particular HMF. If a Lewis acid catalyst is used, the process comprises isomerization of glucose into fructose and conversion of fructose into a furanic compound, in particular HMF.

These reaction conditions generally involve high temperature, high pressure, and/or the presence of an acid catalyst. The reaction conditions may for example involve a temperature between 50 and 300° C., more preferably between 100 and 300° C., such as between 150 and 270° C., in the presence of an acid catalyst. The pressure is preferably at least 2 bar, at least 5 bar, or at least 10 bar, or even at least 20 or at least 30 bar.

The acid catalyst generally comprises a Brønsted acid. Homogenous Brønsted acid catalysts are preferred, for instance in view of use in a continuous process and in view of feed materials comprising non-carbohydrate solid material which remains present in the product stream. Homogenous Brønsted acid catalysts are liquid and/or dissolve in the reactive phase. The catalyst is for instance not a solid material, e.g. suspended in a liquid phase. Mineral acids and carboxylic acids can for example be used as homogenous catalysts.

Suitable Brønsted acids include mineral acids, carboxylic acids, solid acid catalysts, zeolites, and combinations thereof. Strong acids are preferred. Mineral acids can suitably be used. Sulfuric acid, nitric acid and phosphoric acid are preferred. In case of a solid acid catalyst, strongly acidic ion exchange resin particles can for example be used, such as cross-linked polystyrene containing sulfonic acid groups.

A Lewis acid catalyst, for example a metal salt, may in addition be used, in particular for the conversion of glucose into fructose. A Lewis acid catalyst can for example comprise a transition metal, a lanthanide metal, or a metal selected from Groups 4, 5, 13, 14, and 15 of the periodic table of elements. Halides of such salts are preferred, for example chlorides, such as $AlCl_3$.

The reaction medium preferably has a pH of less than 4, or less than 3, or less than 2, for example from 1.0 to 2.5, or from 1.0 to 2.0. The reaction medium may for instance comprise at least 0.1 wt. %, or at least 0.3 wt. % $H_2SO_4$ and conjugated base, based on weight of the reaction medium. The reaction medium may comprise for example at least 5 wt. % water, or at least 10 wt. % water, based on the liquid components of the reaction medium.

The process comprises subjecting feed material to reaction conditions in a reaction medium comprising two immiscible liquid phases, including a reactive phase and an extractive phase.

Advantageously, in the process, the reaction conditions cause the opening of the solid component, hydrolysis of polysaccharides to yield monosaccharides, and dehydration of said monosaccharides in a single reaction medium, in particular in a single reactor.

The extractive phase comprises an organic solvent, preferably a nonpolar solvent, preferably for at least 80 wt. % or at least 90 wt. % based on liquid components of the extractive phase. The extractive phase is for example capable of dissolving less than 25 wt. % water, preferably less than 5 wt. %, based on total weight of the organic solvents of the extractive phase.

The extractive phase may for example comprise one or more organic solvents, such as straight, branched and cyclic aliphatic hydrocarbons, such as alkanes and cycloalkanes, and aromatic hydrocarbons. The aliphatic hydrocarbons may have for example from 3 to 12 carbon atoms. The aromatic hydrocarbons may have for example 6-12 or 6-8 carbon atoms. Optionally, the aliphatic or aromatic hydrocarbons may be substituted, for example with at least one halogen atom and/or with a heteroatom group comprising for example O, N, S, or P, such as nitriles, hydroxyl, alkoxy, amine, amide, ether and esters. Also suitable are polyether solvents.

Preferably, the solvent is an alkylphenol or alkoxyphenol, preferably with an alkyl or alkoxy group with 1, 2, 3, 4, or 5 carbon atoms, for example at the 2-position.

Suitable solvents include for example 1-butanol, 2-sec-butylphenol and methyl isobutyl ketone, 2-butanone, guaiacol (2-methoxyphenol), and 2-methyltetrahydrofuraan. In an interesting embodiment, the organic solvent is guaiacol, but the invention is not restricted to this solvent or to alkoxyphenol as solvent. These solvents may provide particularly good results with a solvent:reactive phase mass ratio above 2.5:1, for example in a ratio of about 3:1, wherein the reactive phase liquid preferably is water, and more preferably with a pH in the range of 1-2, even more preferably a pH of about 1. In a batch experiment, a yield of >30 mol % HMF was obtained for guaiacol as organic phase with 100 g/l sieve fraction feed material, a water:guaiacol ratio of 1:3, HCl as acid catalyst, pH 1, at 200° C. for a 45 min, with in addition >10 mol % furfural and about 25 mol % glucose.

In some embodiments of the invention, these solvents are used in a biphasic reaction medium, wherein the process is a continuous process or a batch process for the production of HMF and/or furfural from biomass, optionally with a reaction medium not comprising a solid component.

The extractive phase preferably has a water content of less than 10 wt. %, more preferably of less than 5 wt. %, just before adding together with the reactive phase. The reactive phase comprises water, preferably at least 1 wt. % or at least 10 wt. % or at least 50 wt. %, or at least 90 wt. % water, based on the total weight of the liquid components of the reactive phase. Preferably the reactive phase is aqueous. Optionally, the reactive phase comprises, in addition to water, one or more water-miscible organic co-solvents, for example in a mass ratio of less than 3:1 or less than 2:1 or less than 1:1 (co-solvents:water).

Optionally, the reactive phase comprises a modifier such as an organic solvent that has for example a high boiling point, is polar, and/or is aprotic, for example DMSO (dimethyl sulfoxide), for example in a mass ratio of up to 2:1(total modifiers:water).

Preferably, the mass ratio between extractive phase and reactive phase in the reaction medium is at least 1:2 or at least 1:1 or at least 3:2, at least 2:1, at least 2.5:1 or at least 3:1 (extractive phase:reactive phase), based on weight of the liquid components.

The process involves dehydration of glucose and/or fructose into furanic compounds, and extraction of the formed furanic compounds by transfer of formed furanic compounds from the reactive phase into the extractive phase through an interface between said phases. In particular HMF is preferably continuously extracted from an aqueous reactive phase into an organic extractive phase. The present application provides in an aspect the judicious insight that use of a pulsed column reactor contributes to the conditions for such continuous extraction.

Said dehydration and extraction take place, for at least a part, simultaneously within a multiphasic reaction medium. The two liquid phases are immiscible, such that under reaction conditions (temperature and pressure) the phases are separated in equilibrium. Usually, the immiscible liquid phases have interfacial contact in said reaction step, in particular the reactive and extractive phase. The process also generally involves hydrolysis of a polysaccharide into at least glucose and/or fructose, prior to or simultaneously with the dehydration.

In the preferred process of the present invention, the reaction medium comprises said two immiscible liquid phases and further comprises a solid material component comprising at least a part of a carbohydrate-containing fraction of the feed material. In some embodiments, the solid components are particles or pieces of the feed material. The solid component preferably comprises polysaccharides. In some embodiments the pre-treatment comprises separating a carbohydrate-containing fraction from at least one other fraction of the feed material. In other embodiments, the reaction medium comprises a solid component comprising at least a part of a carbohydrate-containing fraction of the feed material which is not separated from other fractions of the feed material. Preferably, the reaction medium is a slurry comprising a biphasic liquid reaction medium and suspended particles of feed material or at least a fraction of feed material. The stream obtained from the outlet of the reactor optionally comprises feed material particles as feed residue, but at least part of the carbohydrate provided in such particles at the inlet is converted by the reaction during transport of feed material to the outlet of the reactor.

In the preferred process, the reaction medium at an inlet of the reactor optionally comprises dissolved monosaccharides obtained from a recycle stream.

The process is a continuous process, wherein at least one of the process steps is carried out in a continuous or semi-batch manner. In particular the process step wherein furanic compounds are obtained by dehydration of a monosaccharide is carried out as a continuous or semi-batch step in a reactor. Typically, the reaction medium at the outlet of the reactor comprises non-reacted polysaccharides and monosaccharides. These are optionally recovered from the reaction medium and recycled into the reactor.

The reactor wherein furanic compounds are formed is configured for continuous or semi-batch processes. Accordingly, in the process, a stream comprising said particles is continuously introduced into a reactor through an inlet of the reactor, and at least one stream is continuously and simultaneously withdrawn through an outlet of said reactor, wherein said inlet and outlet are spaced apart. Preferably, the reactor is a tubular reactor, a column reactor, or a continuously stirred tank reactor. Optionally, a plurality of reactors is used for instance with different types of reactors in series.

In some embodiments, the reaction medium is well mixed in the reactor. In an interesting embodiment, the two liquid phases are mixed in the reactor. In the reactor, one of the liquid phases is for example dispersed in the other phase. For instance, the reactive phase is dispersed in the extractive phase, in particular the heavy aqueous phase is dispersed in the light organic phase. The solid component may for example be present as a slurry in the reactive phase and an organic extractive phase can be added to form a reaction medium.

Preferably, the reaction medium is agitated in the reactor to ensure sufficient mixing of the liquid phases and to prevent sedimentation of solids in the reactor. Preferably, the reactor is configured for facilitating mixing of a slurry comprising biomass, an aqueous and an organic liquid phase, and the catalyst, wherein the biomass is provided as solid material. Preferably, the reactor is configured for continuous transport of components of the reaction medium through the reactor from an inlet to an outlet, for example for continuous transport of the liquid phases to respective outlets. The reactor is preferably configured for transport of solid components, in particular solid biomass particles and pieces, from an inlet in the direction of an outlet. Depending on the extent of the conversion, only a small amount of the solid biomass, or none, may reach the outlet. Preferably, the process involves flow of biomass particles in said reaction medium in said reactor from an inlet in the direction of an outlet.

A column reactor is particularly preferred. The column reactor can have any orientation, e.g. horizontal, diagonal, or vertical. A column reactor for example comprises a vertically extending vessel, such that the ends of the column are vertically spaced apart (including oblique). Preferably, the at least two immiscible phases of the reaction medium are in counter-current flow in the reactor. Co-current flow is also possible. Typically each end of the column is provided with an inlet and an outlet. Preferably, at either end or both ends, the outlet is positioned closer to the end than the inlet, so as to provide a settling section. Preferably, the process involves coalescence of the dispersed phase in such settling section, progressing of the phase separation, and selectively withdrawing one of the phases, e.g. by pouring, from the settling section.

Preferably, the organic phase is the light phase and the aqueous or reactive phase is heavy phase (i.e. having higher mass density). The light phase is introduced through an inlet at the bottom and withdrawn through an outlet at the top, the heavy phase is introduced through an inlet at the top and withdrawn through an inlet at the bottom. Either the heavy phase or the light phase is dispersed in the other phase. Preferably at least one of the inlets is provided with a liquid distributor for introducing droplets of the dispersed liquid phase into the reaction medium.

Preferably, the column is provided with baffles, discs, perforated plates, and/or annular rings over at least part, such as over a majority, of the length of the column, and preferably mounted on or attached to the vessel of the column.

Preferably, the reactor is a mechanically agitated column. Preferably, the column reactor contains an agitation unit. Optionally, the agitation unit comprises at least one shaft extending in the vertical direction, wherein the shaft is provided with for example agitators, baffles, and/or impellers, and wherein in operation the shaft rotates and/or is reciprocated. Preferably the shaft is at one end coupled to a drive mechanism for reciprocating and/or rotating movement of the shaft. In an embodiment, the reactor is a reciprocating-plate extraction column. Such column is particularly advantageous for liquids with suspended solids. For example the Karr reciprocating-plate extractor can be used, comprising a column with a stack of perforated plates mounted on a shaft which is coupled with a reciprocating drive mechanism for reciprocating movement of the shaft and the plates.

In some embodiments, packed columns are used. Such columns comprise for example a structured packing and liquid distributors for the two liquid phases. The liquid distributors are usually arranged for counter-current flow of the liquid phases. The liquid distributors are generally configured for distributing the liquid over the whole cross sectional area of the column. They generally allow for introduction of a liquid as droplets. The packed column preferably comprises a structured packing. Suitable packings include in particular packings constructed of metal pieces such as metal sheets.

In particular for column reactors, a homogenous acid catalyst is preferred. In this way, the acid catalyst can be continuously refreshed and catalyst inactivation is avoided. The column reactor optionally does not include a fixed bed. Optionally, no bed of catalyst particles present in the column. Optionally, the reaction medium in the reactor does not comprise catalyst particles. Optionally, the reaction medium in a reactor comprises cellulose fibres and an acid catalyst, such that the catalyst can interact with the fibres. By optionally not using a fixed bed and/or solid catalyst, deposition of humic material on the solid catalysts and/or packed bed can be reduced.

In a preferred embodiment, the feed material comprises a polysaccharide and the reaction conditions are applied to the polysaccharide in a reactor, preferably a column reactor. The at least two immiscible liquid phases have interfacial contact in the reactor and these phases are in co-current or counter-current flow. The particles comprising the polysaccharides are dispersed in at least one of said liquid phases of the reaction medium in the reactor and flow from an inlet towards an outlet of the reactor. More preferably, the Brønsted acid catalyst is a homogenous acid. The reaction conditions cause the opening of the solid component, hydrolysis of polysaccharides to yield monosaccharides, and dehydration of said monosaccharides in a single reaction medium. The reaction conditions preferably comprise a temperature of at least 150° C. and a pH of 2 or less. This combination of features is particularly advantageous for heterogeneous feed streams.

Preferably, the process uses a pulsed column reactor, wherein a reciprocating movement is applied to the reaction medium, such that the reaction medium, in particular the liquid phases, has alternatingly forward and backward flow and e.g. in case of a vertical reactor (including oblique) moves alternatingly up and down in the column. Accordingly, preferably an oscillating flow is provided in the reactor. Herein, forward means flow from inlet to outlet, and backward means flow from outlet to inlet. Preferably, the inlets and outlets of the reactor are arranged at opposed ends of the reactor.

Preferably, the reaction medium has a reciprocating upward and downward flow (forward and back flow) during said reaction step. Preferably, a reciprocating forward and backward flow (upward and downward flow) of the reaction medium is added to the net flow of the liquid phases during said reaction step. More preferably, a sinusoidal back and forth flow (up-and-down flow) is superimposed. Optionally, the flow ratio between the superimposed flow and the net flow is in the range of at least 5 and e.g. up to 6000, preferably at least 20 and e.g. up to 60 (e.g. in $m^3/h$). The ratio between the maximum oscillatory flow rate and net flow rate is for example more than 1, or at least 2, preferably at least 5 or at least 10. The ratio is typically less than 80, for instance less than 40. The frequency of the oscillations is for instance more than 0.05 Hz and less than 10 Hz, e.g. at least 0.10 Hz, at least 0.2 Hz or at least 0.5 Hz, and e.g. less than 2 Hz, such as in the range 0.1-1 Hz. The flow oscillations or pulsed flow for instance provide for a pressure fluctuation of at least 2 bar, at least 5 bar or at least 7 bar, such as around the operating pressure. The operating pressure is e.g. at least 10 bar, at least 15 bar, or at least 20 bar. The temperature of the reactor is for instance at least 110° C., at least 130° C. or at least 150° C. The pulsed column, e.g. oscillating baffled column reactor, is for instance supplied with a feed liquid comprising at least 0.10% w/w/fibers, or at least 0.20% w/w, based on weight of the reaction medium. The volume ratio between aqueous phase and organic phase, preferably apolar organic phase, is for instance in the range 1:10 to 10:1, preferably 4:1 to 1:4. Such volume ratio contributes to good product extraction.

A pulsed column reactor is provided with a pulsing device, typically in fluid connection with the reaction medium in use, to provide such a reciprocating movement to the reaction medium. Examples include a mechanical pulsing device and a fluid-operated pulsing device. In this way, an advantageous level of mixing of the components of the reaction medium can be obtained since mass flow and retention time are decoupled. For example an air-pulsed column can be used, wherein the column is provided with a tube having at one end a valve for introducing and withdrawing liquid (i.e. a leg). In the process, air is introduced and alternatingly withdrawn at one end of the tube using for instance a solenoid valve, the other end has an opening and is in liquid contact with the reaction medium. Also possible is providing at least one liquid phase, or both, in a pulsed fashion, in particular by applying reciprocating movement to the liquid phase upstream of the inlet to the reactor. A reciprocating member, in particular a reciprocating piston, in fluid connection with the reaction medium may also be used. The reciprocating member is in particular in liquid connection with the reaction medium. In principle, any of the mentioned reactors may use a pulsing device to provide pulsed flow of the reaction medium in the reactor.

The pulsed column reactor is preferably equipped with structures protruding the flow (for example, baffles, static mixers of any kind, like rings, twisted plate inserts, corrugated sheets, or unstructured packing material). Such protruding structures advantageously break up flow patterns and create vortices that enhance mixing in the column.

The use of a pulsed column advantageously allows for the solid particles comprising at least a carbohydrate-containing fraction of the feed material to be in suspension in the liquid phases of the reaction medium. The pulsed column also contributes to the continuous extraction of products from the reactive liquid phase to the extractive liquid phase by ensuring mixing and interfacial contact between these liquid phases.

In addition, mixer-settlers and mixer-settler columns can be used. A mixer-settler comprises a mixing unit with at least an inlet and a downstream settling unit with separate outlets for light and heavy phase. Multiple units can be arranged alternatingly in series. A mixing unit may comprise an impeller on a rotating shaft for dispersing the liquid phases. A mixer-settler column comprises a plurality of stages on top of each other in the column, each stage comprising a mixing zone and a settling zone. The stages are hydraulically separated. This allows for stage-wise contact and long phase separation times.

In a preferred embodiment, the reactor comprises multiple zones, wherein the reaction conditions in at least some zones are controllable independently of at least some other zones, in particular adjacent zones. The zones are preferably arranged in series for the flow of the reaction medium. The zones are preferably operated as having different pressure, temperature, pH and/or composition of the reaction medium. In a preferred embodiment, a reactor having multiple zones has a single vessel having multiple zones. The use of different zones may advantageously allow for opening-up of biomass, hydrolysis and dehydration to be carried out in a single reactor having multiple zones.

Preferably, the reactor is a tubular reactor or a screw reactor, such as a twin screw reactor, preferably having multiple zones. In a preferred embodiment, the reaction conditions are applied in a plug flow reactor, such as a tubular reactor, wherein said reactor is configured and/or operated to maintain plug flow. Preferably the reactor has multiple zones. In a further embodiment, a spinning disc reactor is used, with for example one or more disks on a common spindle in a cylinder, more in particular a rotor-stator spinning disk reactor with for example stators between the disks.

The process generally comprises one or more steps downstream of the production of furanic compounds which are applied to a liquid stream comprising the furanic compounds. The downstream steps generally include product isolation and purification. The process accordingly is preferably carried out in a system comprising a downstream section that is provided downstream of the reactor, in particular downstream of the outlet of said reactor for reaction mixture or for the organic extract phase. The downstream section preferably comprises a separation unit, optionally a plurality of separation units in series. The separation units are preferably operated in a continuous manner.

Preferably, the downstream section comprises a solid/liquid separation unit, such as a filter, for example for removal of any unreacted solid feed material, or of any solid material formed during the reaction. This is in particular useful to remove any formed humic material, especially for humin compounds which are generally insoluble and may be present as suspended solid material in a stream obtained from the reactor. In an interesting embodiment, humic material is separated from the reaction medium, optionally purified, obtained and collected as product. The humic material product can for example be used as fuel. An advantageous approach to valorisation of humins comprises pyrolysis at elevated temperatures (e.g. between 300 and 550° C.) to liquefy the product. The liquefied product is easier to transport than the solid humin material and can be used for example as co-feed in power stations or as boiler fuel. In yet a further preferred embodiment, solid material is obtained in the solid/liquid separation and is used in a valorisation process. For example lignin may be isolated from the separated solid material and obtained as product. Any solid component separated from the stream obtained from the reactor may for instance be used as fuel.

Preferably, the downstream section comprises a liquid/liquid phase separation unit for separating the liquid phases from each other, more preferably downstream of the solid/liquid separation. The liquid/liquid phase separation unit can for example use the difference in volumetric mass density between the liquid phases, such as by centrifugation. Such a phase separation unit may be used in addition to any phase separation zones in the reactor. Optionally, the phase separation unit is used in combination with a column reactor having phase separation zones at least at one end. The separated aqueous phase is optionally recycled to the reactor, for example after purification. The recycle stream optionally comprises dissolved mono and oligo saccharides, solid feed material residue and acid catalyst. The separated aqueous phase and/or separated solid material may also at least in part be subjected to one or more post-treatment steps to enable utilization of components contained therein, for example for the production of compost or biogas. Similarly, a stream of the aqueous phase withdrawn separately from the reactor may also be purified and recycled to the reactor.

The separated extractive phase comprising the formed furanic compounds is usually subjected to one or more product recovery steps for isolation and recovery of the product. These may comprise for instance cooling, neutralization, inducing precipitation, crystallization, adsorption, liquid-liquid extraction and purification such as distillation or recrystallization. The organic solvent is usually recovered and recycled to the reactor, optionally after a drying step.

The downstream section may for example comprise one or more downstream processing units or reactors, generally downstream of the solid/liquid separation unit and liquid/liquid phase separation unit, configured for receiving at least part of the separated organic phase comprising the formed furanic compounds, or for receiving a stream comprising the formed furanic compounds, for instance downstream of a back-extraction or extraction step. These reactors are for example provided with an inlet for reagents and/or catalyst and an inlet for said organic phase, and preferably with an agitator such as stirrer, and a heater or heat exchanger. Accordingly, the process preferably comprises, downstream of the reaction step wherein furanic compounds are formed, one or more downstream processing steps. These downstream processing steps are preferably downstream of the liquid/liquid separation and/or solid/liquid separation step.

Preferably, the one or more downstream processing steps comprise a step wherein the formed furanic compounds are subjected to one or more chemical reactions, more preferably in at least part of said organic extractive phase and/or in a downstream treatment unit in fluid connection with said reactor. Generally, said formed furanic compounds are not isolated and are maintained in a liquid medium (preferably the organic extractive phase) from the reactor to said downstream processing step. In this way, the downstream processing steps may provide for telescoping of the reaction. For example, the steps are telescoping steps such as carried out by adding reagents and providing catalysts to the reactor effluent subsequent to filtration and phase separation to provide an organic phase used as feed for a downstream treatment unit. The phase separation for example comprises liquid-liquid phase separation of the two immiscible phases of the reaction medium, e.g. liquid-liquid separation of the organic phase and aqueous phase. The separation can be carried out using a separation method based on a difference in mass density of the liquid phases, such as settling or with centrifugal separation, e.g. with a hydrocyclone. Typically, the one or more downstream processing steps are carried out as continuous process steps, e.g. in a reactor unit with an inlet and an outlet. The reactor unit can for example be a tubular reactor, a column reactor, or a continuously stirred tank reactor. In case the reactor for the formation of furanic compounds is a pulsed column reactor, then the process preferably comprises a flow rectifying step to convert the oscillating flow into a substantially plug flow, or non-oscillating flow (i.e. forward only flow). The stream with plug flow or non-oscillating flow is then supplied to the one or more downstream processing steps, for instance in a flow rectifying unit such as an overflow or a flow regulating valve.

Preferably, the chemical reaction is selected from the group consisting of reduction, hydrogenation, oxidation, esterification, amidation and/or condensation.

Preferably, an aldehyde group of a formed furanic compound is reacted. For example, furfural and/or HMF can be subjected to one or more telescoping reactions, including condensation reactions, such as with hydrazine and/or hydroxylamine.

Preferably, a furanic compound such as HMF and/or furfural is oxidized to yield 2,5-furandicarboxylic acid (FDCA) and/or 2-furoic acid. More preferably, the process comprises conducting an oxidation of a furanic compound, such as HMF and/or furfural, to yield FDCA and/or 2-furoic acid and an esterification reaction of FDCA and/or 2-furoic acid with an alcohol, preferably in the same reaction medium, to provide an ester of FDCA and/or 2-furoic acid. Preferably the ester is a dialkyl ester, wherein said alkyl group preferably has 1 to 12 carbon atoms, more preferably dimethyl, diethyl, di-propyl or di-butyl ester of FDCA and/or of 2-furoic acid. In situ esterification of FDCA is particularly advantageous because the ester intermediate is more readily distilled than FDCA. Recovery of FDCA from water or solvents is cumbersome, while the further purification is difficult because of the extremely high melting and boiling points. Preferably, the process comprises distillation of the ester. Such FDCA ester is an attractive starting material for polymerization reactions.

Optionally, the process comprises hydrogenation of HMF into dimethyl-furan (DMF) or to 2,5-bishydroxymethyl-furan, or oxidation to 2,5-diformylfuran or an acetalization reaction of HMF with a diol. Optionally, the process comprises hydrogenation of furfural into 2-methylfuran or to 2-hydroxymethyl-furan, or an acetalization reaction of furfural with a diol. HMF and/or furfural may also be hydrogenated to yield a ring-opening product. Hydrogenation of HMF and/or furfural is particularly advantageous because DMF and 2-methylfuran are more readily distilled. The process may also comprise a Wittig reaction of HMF and/or furfural to yield a vinyl furan. Preferably, the process comprises conversion of an aldehyde to an alcohol, for example to provide 2,5-bishydroxymethyl-furan and/or 2-hydroxymethyl-furan.

Such downstream processing steps, in particular when carried out as telescoping steps, advantageously facilitate product recovery and recycle of the organic extractive liquid phase, e.g. of an organic solvent used for the extractive liquid phase. In a preferred embodiment, the process comprises one or more of such downstream processing steps, recovery of the product, e.g. reacted furanic compounds, such as aromatic compounds, from the organic liquid, and recycling the organic liquid phase, depleted in the products, to the preferably pulsed column reactor for the formation of furanic compounds or a unit upstream of said reactor.

These downstream processing steps can also be used for embodiments wherein the pre-treated feed stream is homogenous, e.g. a solution, and/or wherein a monophasic reaction medium is used, and/or wherein the feed material does not contain a solid component. Accordingly, yet a further aspect of the invention pertains to a biomass conversion method comprising a step wherein biomass is converted into furanic compounds, and one or more of said downstream processing steps. Preferably, the method comprises the reaction of the formed furanic compounds with a hydrazine and/or hydroxylamine as described elsewhere in this application, or the oxidation and esterification to provide an ester of FDCA.

The process is generally for the conversion of a material into furanic compounds. The process is in particular for the production of HMF and/or furfural. Preferably, at least HMF and furfural are formed in the reaction medium.

More generally, the obtained furanic compound as present in the reaction medium and/or in the organic phase, optionally after said downstream processing steps, has a formula according to formula I

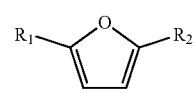

I wherein $R_1$ and $R_2$ are independently selected from the group consisting of heteroatoms, halogens or linear or branched $C_1$-$C_8$-alkyls, optionally substituted with halogens and/or substituted with and/or comprising heteroatoms. More preferably, $R_1$ and $R_2$ are independently selected from the group consisting of H, Me, F, Cl, Br, I, —CHO, —CH$_2$F, —CH$_2$Cl, —CH$_2$Br, —CH$_2$I, —CN, —NO$_2$, —CH$_2$NH$_2$ and amides thereof, —CH$_2$OH and esters or ethers thereof and —CO$_2$H and esters thereof. Preferably, $R_2$ is —CHO and $R_1$ is —CH$_2$F, —CH$_2$Cl, —CH$_2$Br, —CH$_2$I, —CN, —CH$_2$NH$_2$ and amides thereof, —CH$_2$OH and esters or ethers thereof, in particular alkyl esters, more in particular methyl, ethyl, propyl and butyl esters.

Optionally, the process comprises one or more downstream steps wherein the furanic compound is reacted with a dienophile, in particular an alkene or alkyne, to give an aromatic compound comprising a benzene ring. Such cycloaddition reactions with aromatization of furanic compounds are well-known as such. The dienophile preferably comprises one or more electron withdrawing groups (EWG) attached to a carbon atom having a double or triple bond. Preferably, EWG=—CN, —NO$_2$, —CO$_2$X, —C(O)NX, —C(=NY)X, CF$_3$, CCl$_3$CBr$_3$, CI$_3$, —SO$_2$X, —SO$_3$X, —COH, —COX, —COF, —COCl, —COBr, —COI, wherein X and Y are independently H, or linear or branched C$_1$-C$_8$-alkyl, optionally substituted with halogens and optionally polymer-supported. Alkene dienophiles common in the art may be used, for instance selected from the group consisting of acrylonitrile, maleic anhydride, maleimide, citraconimide, dimethyl fumarate, dimethyl acetylenedicarboxylate, 3-buten-2-one, 1,4-benzoquinone, allyl chloride, maleic acid, itaconic acid, aconitic acid, acrylic acid, crotonic acid, isocrotonic acid, methacrylic acid, tiglic acid, acetylene dicarboxylic methyl ester, vinyl acetate, and esters of maleic and fumaric acids, for example dimethyl maleate and dimethyl fumarate, and alkyl esters of any of such acids. The dienophile can for example be maleic anhydride. In a preferred embodiment, the dienophile is an N-alkylmaleimide, such as N-ethylmaleimide.

The reaction with a dienophile is preferably catalyzed, preferably with a protic or a Lewis acid, more preferably with a Lewis acid, even more preferably with a Lewis acid based on a metal. Preferably the catalyst is a complex or salt of a metal selected from the group consisting of Zn, Al, Sc, B, Fe, Ir, In, Hf, Sn, Ti, Yb, Sm, Cr, Co, Ni, Pb, Cu, Ag, Au, Tl, Hg, Pd, Cd, Pt, Rh, Ru, La, Ce, Pr, Nd, Pm, Eu, Gd, Tb, Dy, Ho, Er, Tm, Lu, V, Mn, Y, Zr, Nb, Mo, Ta, W, Re, Os.

In an interesting embodiment, the formed aldehyde-containing furanic compounds, in particular furfural (FF) and HMF are subjected to a condensation reaction with a hydrazine and/or hydroxylamine as downstream processing step, to provide hydrazone and/or oxime compounds, in particular in an organic phase. Hence, the process preferably comprises such a reaction as telescoping step. For instance, the reactor effluent from a reactor for the furanic formation is subjection optionally to filtration and to liquid/liquid separation, to separate the organic phase containing furanic compounds from at least part of the aqueous phase. The organic phase is preferably subjected in a continuous process to such condensation reaction by addition of hydrazine and/or hydroxylamine in a downstream continuous reactor unit, typically with plug flow. If necessary, the pH of the organic phase can be increased, e.g. by addition of an alkaline compound, prior to the reaction with hydrazine and/or hydroxylamine.

Usually, the hydrazine and hydroxylamine compounds are modified with an organic group at one end. The formed furanic hydrazone and oxime compounds are less prone to take part in side reactions. The compounds are also activated for a reaction with a dienophile as described to form aromatic compounds. Such a reaction with a dienophile is preferably carried out by adding the dienophile to the effluent from the reaction with hydrazine and/or hydroxylamine compound, preferably as further telescoping step.

In a preferred embodiment, the liquid stream comprising the formed furanic compounds and at least part of the organic extractive liquid phase is supplied from an outlet of the reactor to an inlet of a downstream processing unit wherein at least the hydrazine and/or hydroxylamine are added into said liquid stream. Preferably, the reactor is a pulsed column reactor. Preferably the reaction medium has a reciprocating forward and backward flow, or oscillating flow, in the pulsed column reactor. Preferably the process comprises converting the oscillating flow or reciprocating of the stream or of the reaction medium into forward only flow upstream of the inlet of said unit, such as between the pulsed column reactor and said inlet, e.g. at the outlet of the pulsed column reactor.

Advantageously, by converting the aldehyde group into a hydrazone or oxime group, the oxidation state of the carbon atom of the aldehyde group is not altered while elegantly the hydrazone or oxime group is electron-donating. In this way, the reaction with the dienophile and ring opening may be enabled or promoted, and the aldehyde functionality can be restored in the aromatic product without oxidation, using for example hydrolysis. A further oxidation of the aldehyde to hydroxyl or carboxylic acid can be relatively mild, and likewise oxidation of a hemiacetal to ester.

Particularly attractive is the reaction of the aldehyde-containing furanic compounds with supported hydrazine and hydroxylamine compounds which are bound to a solid support, such as a resin, for example in the form of resin beads. Hence, preferably a hydrazine or hydroxylamine bound to a heterogeneous support is used. For example polystyrene resins can be used. Various polymer-bound hydrazine compounds are commercially available. By using such compounds, in particular HMF and furfural are immobilized on the solid support. The solid support-bound furanic compounds can be separated from the organic phase by solid/liquid separation. Subsequently, the organic liquid phase can be recycled to the reactor for the formation of furanic compounds. In this way the solid support-bound furanic compounds facilitate recycling of the organic solvent. The solid support-bound furanic compounds are advantageously easily transferred to another solvent.

Preferably, the process comprises reacting furfural and/or 5-(hydroxymethyl)-2-furaldehyde with a hydrazine and/or hydroxylamine, downstream of said reaction step, wherein preferably the hydrazine and/or hydroxylamine is bound to a solid support, and wherein the process preferably comprises removing said solid support from a liquid medium by solid/liquid separation together with furanic compounds bound to said solid support through a formed hydrazone and/or oxime link.

The furan-hydrazone and/or furan-oxime compound is preferably reacted with a dienophile to provide an aromatic compound comprising a benzene ring and the hydrazone or oxime group.

Optionally, the aromatic compound comprising a benzene ring and a hydrazone or oxime group is subsequently reacted to convert the hydrazone or oxime group into another group, such as an oxygen containing group. For example the hydrazone or oxime group can be converted into a hydroxyl or carboxylic acid group, or ethers, esters or anhydrides thereof, or into an aldehyde or phenol. The hydrazone or oxime group is for instance subjected to hydrolysis, hydrolysis and oxidation, or hydrolysis and decarbonylation.

This downstream processing step involving the use of a hydrazine or hydroxylamine can also be used for embodiments wherein the pre-treated feed stream is a solution, and/or wherein the process is a batch process and/or wherein the reaction medium is a monophasic reaction medium and/or wherein the feed material does not contain solid components.

Accordingly, also provided is a continuous process for the conversion of carbohydrate-containing feed material into furanic compounds, the process comprising:
  a reaction step in a reactor comprising subjecting said feed material to reaction conditions for said conversion in a reaction medium comprising two immiscible liquid phases, including a reactive phase and a preferably organic extractive phase, and a Brønsted acid as catalyst, preferably wherein the reaction medium comprises a solid component comprising at least a part of a carbohydrate-containing fraction of said feed material; and a telescoping step comprises reacting furfural and/or 5-(hydroxymethyl)-2-furaldehyde in at least part of said extractive phase with a hydrazine and/or hydroxylamine, typically in a downstream treatment unit in fluid connection with said reactor. For instance, a hydrazine and/or hydroxylamine is added to or provided in the effluent of the reactor.

In an interesting embodiment, the general process, e.g. of claim 1, comprises modifying the organic solvent comprised in the organic extractive phase. Preferably, the modification provides for enhanced product and/or solvent recovery. Aim of the solvent modification is to facilitate separation of product and solvent. This can be achieved by chemical of physical modification of the solvent. For example butanol can be used as solvent and upon oxidation of this solvent to butanone the solubility of the product changes in such way that a formerly dissolved product becomes insoluble. Also possible is changing physical properties of the environment, such as the pH and/or temperature, resulting in change in interaction between solvent and product and thereby a decreased solubility of the product in the solvent.

Accordingly, a preferred process of the invention is a process for the conversion of biomass into HMF and/or furfural, preferably in a continuous mode, wherein the process design preferably allows for different feed materials. The process preferably comprises performing one or more reactions on the separated extractive phase, such as oxidation, hydrogenation, esterification and/or condensation of the formed furanic compounds. Hence, the process preferably advantageously includes one or more telescoping steps. Such telescoping steps can advantageously improve the efficiency of product formation and/or facilitate separation of product and organic liquid phase (e.g. organic solvent). A preferred telescoping step is a condensation reaction with a hydrazine and/or hydroxylamine, preferably with as subsequent telescoping step a reaction with a dienophile The process can advantageously have relatively short retention times. The process furthermore is particularly adapted for heterogeneous feedstocks, for example by using a preferred pre-treatment and by a preferred column reactor.

Prior art biphasic processes for the production of HMF generally use a monosaccharide solution as feed and a high salt concentration in order to benefit from a salting-out effect and are typically described as lab scale experiments. Such high salt concentration, up to saturation with NaCl, has been reported to provide for an improved partition coefficient for HMF over the reactive and extractive phase.

It has now surprisingly been found that for heterogeneous feeds, lower salt concentrations in fact can give higher yields of HMF. In addition, selectivity is improved because more glucose remains. Hence, in a preferred embodiment, the amount of salts provided into the reactor other than originating from the feed material is maximized to (i.e. the amount is at most) an amount corresponding to less than 2.0 M or less than 1.0 M added cations by volume of the reactive phase, more preferably less than 0.50 M or less than 0.10 M total added cations. In an embodiment, these limits (maximum limits) apply only to metal salts, based on total added metal cations, or only to Na and K salts. In some embodiments, these limits apply to salts added, e.g. salts added to the feed stream upstream of the reactor, or in the reactor, or to any stream provided to the reactor. It was found advantageous to use low salt concentrations and to minimize the amounts of salt added to achieve higher yields of HMF.

FIG. 1 shows the results obtained for conversion of a sewage sieve fraction as feed material in a biphasic system comprising water as reactive phase and 2-sec-butylphenol (SBP) as organic phase in a 1:1 ratio, using 125 mM HCl, for 30 minutes at 195° C. in a batch process and with 0 or 360 g/L NaCl. The HMF yield is higher without salt.

Preferred processes are particularly directed to the utilization of waste streams. Unlike e.g. microcrystalline cellulose which has been used in some research, waste streams are generally heterogeneous streams. Preferably, the feed material is heterogeneous feed material. Heterogeneous material generally comprises a mixture of different chemical compounds. Optionally, heterogeneous material comprises solid particles and/or pieces with a different chemical composition and/or different physical properties, such that the chemical composition is spatially heterogeneous. In particular, the heterogeneous material may comprise parts with a different porosity. Optionally, a heterogeneous material comprises plant matter from at least two or at least three plant species. Optionally, a heterogeneous feed stream is used wherein the composition of the feed stream changes over time during the operation of the process. Optionally, heterogeneous feed material comprises at least 1 wt. % non-biomass material, for example at least 5 wt. %, based on dry weight. Optionally, heterogeneous feed material comprises both solid and liquid components. Heterogeneous feed material may have a combination of these features. These features make the processing of heterogeneous feed material much more demanding than for other feeds. Typically, more severe conditions and/or longer reaction times are required. Use of biphasic reaction medium limits the formation of humins and levulinic acid in aspects of the present invention.

In some embodiments, the feed comprises plant-derived material, preferably lignocellulose. Preferably, the feed comprises plant-based waste material. Examples include vegetable, fruit and garden waste (VFG), agricultural and organic (plant-based) industrial waste.

In some embodiments, the process uses feed material that comprises or essentially consists of waste streams such as solid municipal waste and sewage or fractions thereof. In particular, cellulose-rich fractions from solid municipal waste processing and sewage or wastewater treatment can be used. As a further example, paper waste from the packaging industry can be used, such as from the food packaging industry.

Preferably, the feed material comprises one or more waste materials selected from the group consisting of paper waste, bio-waste (e.g. garden waste, vegetable waste), organic waste, supermarket leftover organic waste, horticulture waste, orange peels, street sweeping waste, a fraction of the organic fraction of municipal solid waste (MSW) (e.g. source separated organics (SSO)), packaging materials, manure, waste from paper production, e.g. black liquor, residual fibers from paper recycling, biorefinery residues, e.g. residue upon digestion, molasses, and biorefinery waste. These are further examples of heterogeneous feed streams. Particularly preferred as feed stream are sieve fractions from sewage treatment and spoiled absorbent articles. In a preferred embodiment, the feed material comprises one or more selected from the group consisting of a sieve fraction from sewage treatment comprising cellulose fibres, a fraction of spoiled absorbent sanitary articles comprising cellulose fibres, and a fraction of manure comprising cellulose fibres. Preferably the reaction medium comprises cellulose fibres.

More in particular, the process preferably uses as feed material components of sanitary articles comprising non-woven cellulose, especially diapers, feminine hygiene products, and incontinence products, which are generally soiled disposable articles, and may be recovered from solid municipal waste. Preferably, the process uses a feed material comprising cellulose mixed with superabsorbent polymers obtained from solid municipal waste or industrial waste. In particular, the filling or absorbent pad of such articles can be used as feed after removal of the covering, e.g. a tissue carrier, and various outer layers. This filling or absorbent pad generally comprises cellulose and superabsorbent polymers as main fractions (e.g. together at least 80 wt. % of the filling or pad), optionally arranged in one or more layers.

The process may also use a sieve fraction from sewage treatment as feed. In particular, generally about 30 to 50% of the suspended solids in sewage consist of cellulose fibres, mainly from toilet paper. It has been proposed to reclaim the suspended solid material using filtration of influent wastewater, e.g. with fine sieves.

The process may also use manure or a fraction thereof from cattle, pig and/or other livestock, optionally upon preferably partial digestion in a biogas production facility. In particular, generally about 10 to 50 wt. % of the suspended solids in manure consist of cellulose fibres. For instance, the manure comprises 10-50 wt. % cellulose fibers based on dry weight. Typically the manure is from livestock.

The use of such filtration with fine sieves results in a (fine) sieve fraction, which is a waste stream with for example a cellulose content of at least 30 wt. % or at least 60 wt. %, or at least 70 wt. %, based on total solids content. Hence, a stream can be obtained that comprises recaptured toilet paper fibres. The filters, such as sieves, which are used for separation of particulate material and cellulose fibres from wastewater may for instance have a mesh size of about 0.35 mm, generally with a mesh size of 500 μm or smaller, preferably larger than 75 μm. Particularly preferred is feed material obtained from filtering with rotating belt sieves. The filter, such as a fine sieve, is generally applied as part of the primary treatment of wastewater and upstream of the secondary treatment comprising contacting the sewage with micro-organisms. The filter may be applied prior to entry of the waste water into a sedimentation tank or settling basin. The filtration may for example be combined with downstream sludge thickening and dewatering to produce a composition comprising cellulose at a dry solids content of for example at least 20 wt. %. The obtained material may comprise e.g. more than 70 wt. % of particles of 5.0 mm or lager, wherein the particles comprise cellulose fibers. A sieve fraction may be provided as feed material as slurry. It is also possible to use sewage sludge, in particular primary sludge, for instance from a primary settling tank, which may for instance comprise at least 20 wt. % cellulose. Also possible is to use as feed material a stream obtained by coarse screening or sieving of wastewater, such as by using screens with openings of at least 2 mm, generally up to 10 mm.

A further aspect of the invention pertains to a reactor system for the conversion of biomass to furanic compounds comprising a reactor comprising an inlet and outlet, wherein the reactor is configured for operation in continuous mode. The reactor is preferably configured for transport of components of the reaction medium from an inlet to an outlet. The reactor system can be used for any kind of carbohydrate-containing feed material, including feed materials containing a solid component as well as feed materials not containing a solid component, e.g. monosaccharide solutions. The downstream processing unit preferably has an inlet that is in fluid connection with an outlet for organic extractive phase of a separation unit, wherein the separation unit is for liquid/liquid phase separation of the reactive and extractive liquid phases. Preferably, the reactor system comprises a flow rectifying unit for conversion of rectifying flow of the reaction medium to forward only flow, e.g. as part of the reactor.

Figure 2:
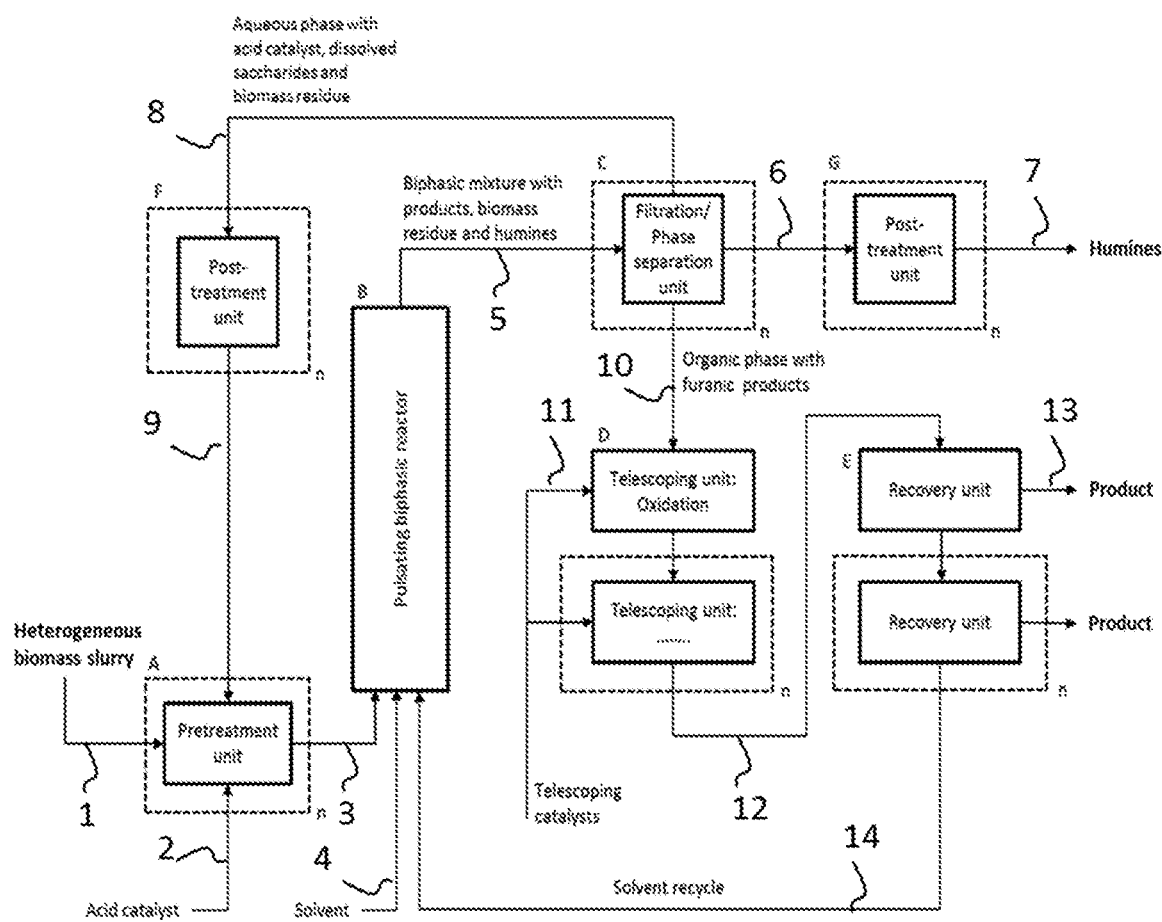
FIG. 2 is a schematic depicting a reactor system according to a non-limiting embodiment of the present invention.

FIG. 2 illustrates a non-limiting embodiment. The reactor system comprises an optional pre-treatment section (A) having an inlet (1) for a heterogeneous biomass slurry as feed material, and an inlet (2) for an acid catalyst and an outlet (3) for a pre-treated feed stream to a pulsating biphasic reactor (B) having an inlet (4) for solvent e.g. organic extractive phase and an outlet (5) for a biphasic mixture with products, biomass residue and humines. Outlet (5) is in connection with one or more separation units (C) including a solid/liquid separation unit (filtration unit) and a liquid/liquid phase separation unit (C). The reactor (B) is optionally coupled to a pulsating device (not shown) in fluid communication with said reactor for providing reciprocating flow to a reaction medium in said reactor (B). The one or more separation units (C) have an outlet (6) for separated solids, such as humic material, non-biomass solid material (e.g. sand) and solid non-polysaccharide biomass material (e.g. lignin) to one or more post-treatment unit (G) having an outlet (7) for solid materials such as a humic material product. One or more separation units (C) also have an outlet (8) for a recycle loop for not completely reacted carbohydrates, e.g. the aqueous phase with acid catalyst, dissolved saccharides and biomass residue. These are supplied to one or more post treatment units (F) having an outlet (9) to the pre-treatment unit (A). Optionally, at least a part of the streams from the outlets 7 and/or 8 is optionally supplied to a composting or biogas unit. The one or more separation units (C) further have an outlet (10) for organic phase with furanic products to one or more optional downstream processing unit (D). These units (D) comprise for example a telescoping unit such as for oxidation and one or more further downstream telescoping units, each having an inlet (11) for telescoping catalysts and/or reagents. The telescoping units (D) have an outlet to one or more product recovery units (E) each having an outlet (13) for product, for instance coupled to a purification unit. The system further comprises a recycle loop (14) for solvent from a recovery unit (E) to the reactor (B). Reactor B can also be a reactor having multiple zones. For inlets and outlets, the respective fluid connection of the reactor system is provided with a label in FIG. 2. Various features described for the process, in particular the reactor, pre-treatment section and downstream section including separation units, product recovery unit and downstream processing unit can be applied for the reactor system. The described processes preferably use the reactor system.

Figure 7:
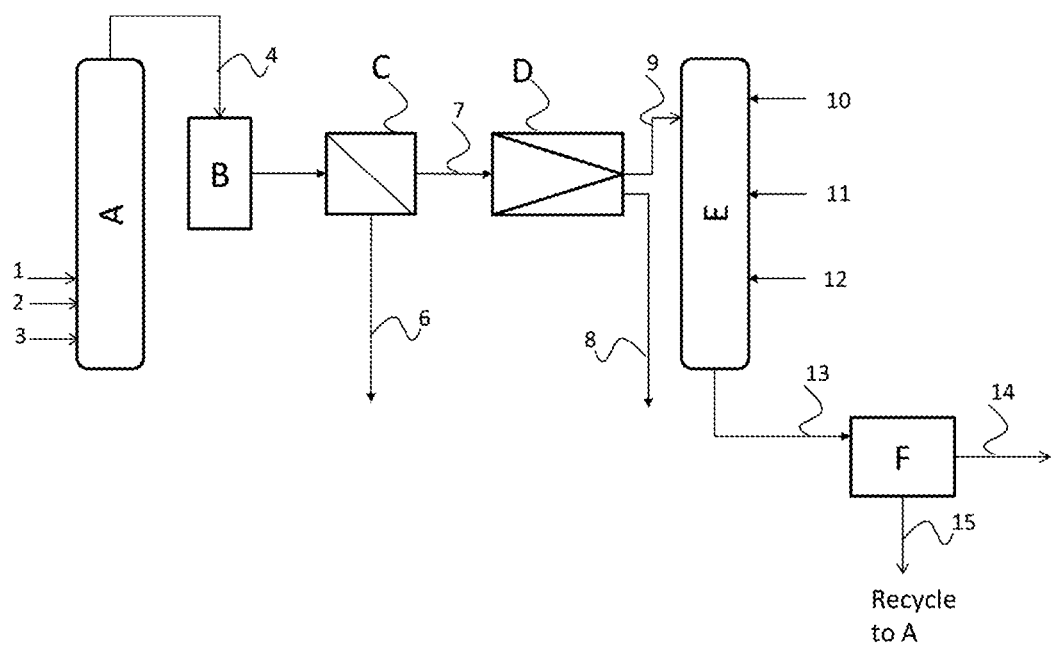
FIG. 7 is a schematic depicting a further example process scheme according to a non-limiting embodiment of the present invention.

FIG. 7 schematically illustrates a further example process scheme which does not limit the invention. The furanic compounds are formed in the reactor A e.g. a pulsed column reactor (which can have any orientation, such as horizontal or vertical as illustrated), receiving a biomass slurry 1, organic solvent 2, and acid catalyst 3 e.g. a liquid or dissolved acid. In reactor A, a biphasic mixture is present, and from an outlet a biphasic stream 4 is obtained. The stream 4 comprises two liquid phases, and additionally solids. This stream 4 is supplied optionally to a flow rectifying unit B for converting pulsating flow (or oscillating flow) to plug flow, e.g. with an overflow or a flow regulating valve. Unit B is optionally and is e.g. placed at some stage between reactor A and downstream processing unit E. The stream 4 comprising an organic and an aqueous liquid phase is supplied to solid/liquid separation unit C, e.g. a filtration unit, giving solids stream 6 (e.g. comprising humins, e.g. as (solid) material) and/or residual biomass solids, and biphasic liquid stream 7. Stream 7 is supplied to liquid/liquid separation unit D, e.g. a hydrocyclone, to separate the aqueous phase as stream 8 from the organic solvent phase as stream 9. The stream 9 comprising furanic compounds and organic solvent is supplied to an inlet of the unit E. Unit E is e.g. a tubular reactor. The unit E is provided, in flow direction, with inlets e.g. for one or more reactants for telescoping reactions. For instance, the unit E is provided with an inlet 10 for base quench, e.g. alkaline solution to increase pH, if necessary, an inlet 11 for hydrazine and/or hydroxylamine, and an inlet 12 for dienophile. The unit E may comprise one or more further inlets for further reactants, e.g. for hydrolysis and optionally oxidation of an aromatic compound comprising a benzene ring and a hydrazone or oxime group. The unit E has an outlet for a product stream 13. The product stream 13 is supplied to a unit F for separation of the product 14, e.g. an aromatic compound, from at least part of the organic phase 15. The separated organic solvent 15 can be supplied at least in part to reactor A, e.g. as part of solvent 2.

EXAMPLES

Example 1: Xylose Conversion in Biphasic Reactor

A 1:1 mixture of 2-sec-butylphenol and 100 g/L xylose solution, which was adjusted to pH 1 with sulfuric acid, was fed to an oscillating baffled reactor with a total flow rate of 5 kg/hr. The mean residence time in the reactor was 30 minutes and the amplitude and frequency of oscillations were 40 mL and 0.16 Hz, respectively. Hence, the ratio between maximum oscillatory flow rate and net flow rate was about 14.5. The temperature of the reactor was 160° C. The oscillations resulted in a pressure fluctuation of about 7.5 bar around the operating pressure of 20 bar. The high pressure was sufficient to prevent boiling of the water phase. Samples were taken every 30 minutes. They were analyzed by means of HPLC analysis and contained about 18% furfural on average. The furfural yield was quite constant over the complete 3 hours of run time (see table 1). This indicates a feasible continuous process for xylose conversion into a furanic compound in a biphasic reactor.

TABLE 1

| Sample | Furfural yield | Residual Xylose |
| --- | --- | --- |
| 1 | 19.9% | 0.3% |
| 2 | 18.0% | 0.4% |
| 3 | 18.2% | 0.4% |
| 4 | 17.1% | 0.4% |
| 5 | 17.9% | 0.4% |
| All samples combined | 20.6% | 0.3% |

Example 2: Pulsed Column with Fibrous Solids

Example 2 illustrates flow experiments with fibrous solids in water and organic solvent/water mixtures.

Figure 3:
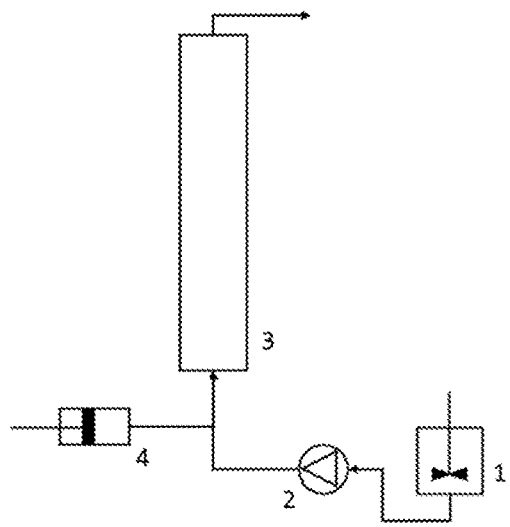
FIG. 3 depicts a schematic representation of the setup in which flow experiments were conducted in a pulsed column of fibrous solids in water.

FIG. 3 shows a schematic representation of the setup in which flow experiments were conducted in a pulsed column of fibrous solids in water. Solid fibrous material of different fiber lengths (d=20 μm, l=60-900 μm) were mixed with water in a stirred supply vessel (1). A pump (2) fed the mixture to the column (3) with flow rates of typically 4-8 L/hr. The column is equipped with structures protruding the flow (for example, baffles, static mixers of any kind, like rings, twisted plate inserts, corrugated sheets, or unstructured packing material) to break up flow patterns and create vortices that enhance mixing in the column. A pulsator (4) superimposed an oscillatory flow onto the net flow rate supplied by the pump. As a result, the mixture moves through the column forward and backward, but with a net positive displacement. The frequency of oscillations was between 0.1 and 4 Hz, the amplitude was between 7 and 42 mL, depending on the fiber concentration and the fibre length. Consequently, the ratio between maximum pulsation flow rate and feed flow rate was for example minimum 1 and maximum 80, preferably between 2 and 40. The concentration of fibers that could be processed was strongly dependent upon the fiber length: the longer the fibers, the lower the concentration needs to be. Concentrations typically between 0 and 5%-w/w were used. Ensuring that the volume percentage of the settled fiber bed was at most 20, provided the advantage of preventing blockage in the lines or in the pump.

Example 3: Pulsed Column and Product Extraction

Example 3 illustrates flow experiments with organic solvent/water mixtures. In the same setup as for Example 2, also experiments were performed with an apolar organic solvent and water. This was done to investigate the conditions needed for the extraction of product from the aqueous phase to an organic phase. It was found that imposing, pulsations in the flow stimulated droplet breakup and increased mass transfer area. It was found that increasing the intensity of the pulsations was best achieved by increasing the pulsation frequency, while limiting the amplitude. This is necessary to maintain a plug-flow like behavior in the reactor, while increasing the power input for droplet breakup. Settings of flow and pulsator were equal to the liquid solid experiments, the volume ratio of water to organic phase was chosen between 1:4 and 4:1.

Example 4: Batch Conversion of Heterogeneous Solid Waste

A pressure tube was mounted with a magnetic stirring bar and filled with given type and amounts of salt, heterogeneous solid waste, acid catalyst and solvent. The tube was sealed with a crimp-cap. The tube was subsequently introduced into a microwave reactor which stirred and heated the reaction mixture at the given temperature and for the given time by means of microwave radiation. After the reaction, the concentrations of monosaccharide, furanics and acids in the aqueous and solvent phase were determined by means of HPLC analysis.

Figure 4:
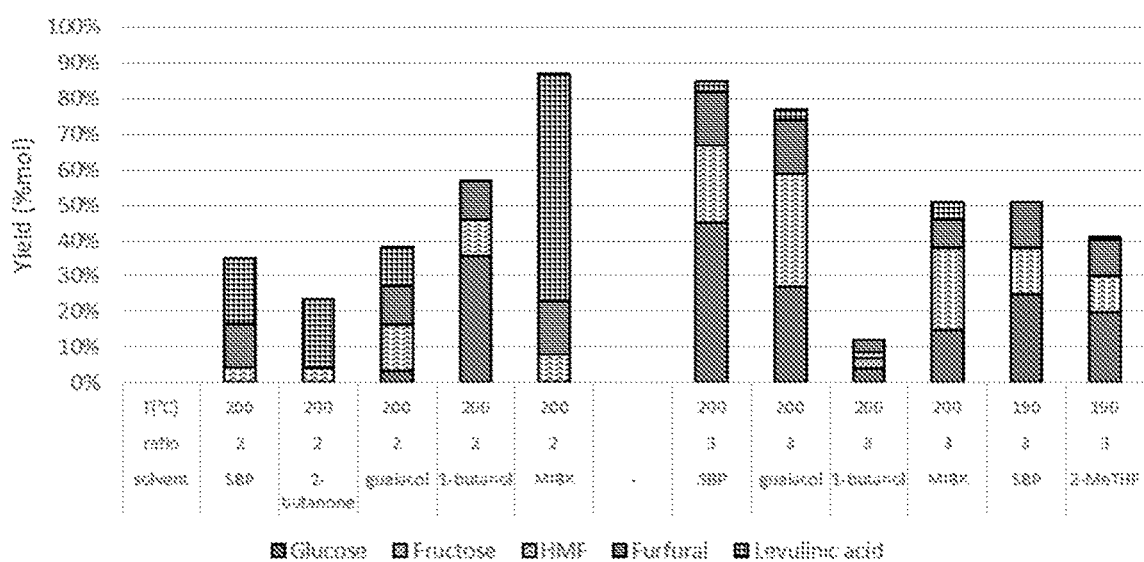
FIG. 4 is a graph showing the obtained yield for the conversion of sewage sieve fraction with different solvents.

FIG. 4 shows the obtained yield for the conversion of sewage sieve fraction with different solvents at the following conditions: 75 g/L sewage sieve fraction, 71 g/L NaCl, reaction volume=3 mL, 100 mM HCl, and reaction times of 22 and 45 minutes. SBP=2-sec-butylphentol, MIBK=methyl iso-butylketone and 2-MeTHF=2-methyl-tetrahydrofuran.

Figure 5:
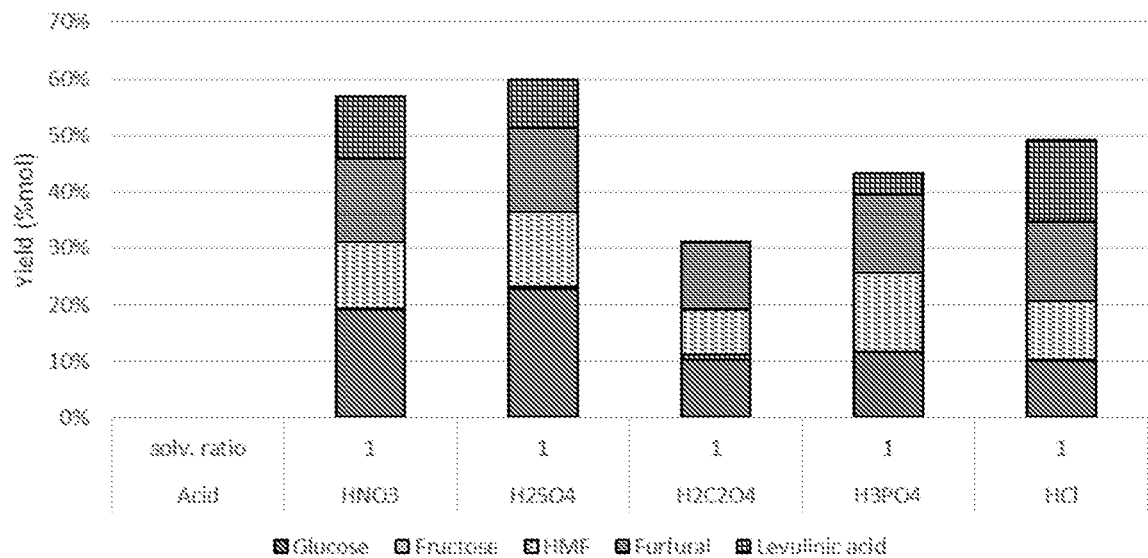
FIG. 5 is a graph showing the conversion of sewage sieve fraction with different acid catalysts.

FIG. 5 shows the conversion of sewage sieve fraction with different acid catalysts at the following conditions: 50 g/L sewage sieve fraction, 71 g/L NaCl, 2-sec-butylphenol: water-ratio=1, reaction volume=3 mL, acid type as indicated at pH 1, 200° C. and reaction time=45 minutes.

Figure 6:
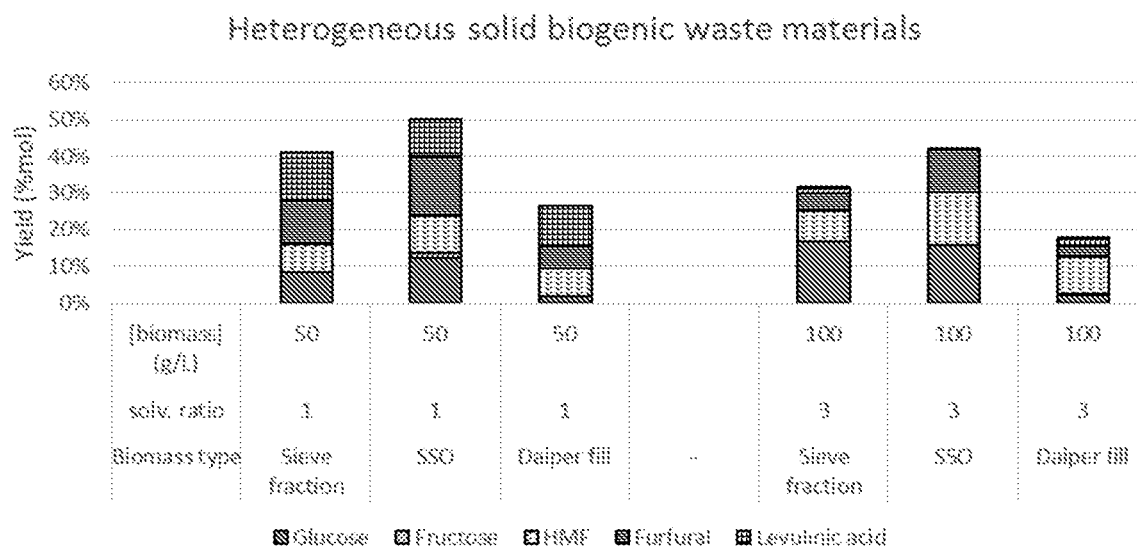
FIG. 6 is a graph showing the conversion with various types of heterogeneous solid biomaterial (biogenic) waste materials.

FIG. 6 illustrates the conversion with various types of heterogeneous solid biomaterial (biogenic) waste materials. The conversion of different heterogeneous solid biogenic waste types is shown for 50 g/L and 100 g/L, 71 g/L NaCl, 2-sec-butylphenol:water-ratios indicated, reaction volume=3 mL, 100 mM HCl, 200° C. and a reaction time of 45 minutes. SSO=source separated organics.

Example 5: Telescoping of HMF Via Hydrazone to Aromatic in 2-Sec-Butylphenol

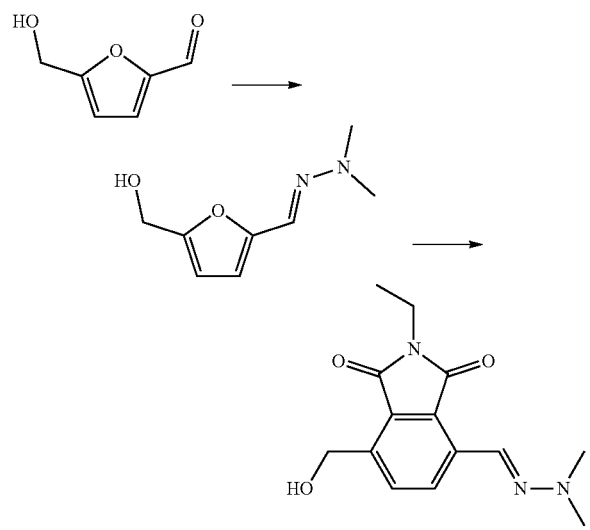

To a reactor was charged 2-sec-butylphenol (8.81 mL) and upon stirring, 5-(hydroxymethyl)furfural (HMF) (2520 mg) and, after 2 minutes, 1,1-dimethylhydrazine (1260 mg, 1600 μL), which was added dropwise. The reaction mixture was stirred at 20° C. for 1 hour, after which the mixture was an orange/brown solution. LCMS analysis at this point revealed nearly complete conversion to the desired hydrazone intermediate. The resulting yellow/brown hydrazone solution was carried through into the following reaction without any further purification/work-up.

To the reactor containing the yellow/brown hydrazone solution was charged N-ethylmaleimide (250.3 mg), whilst stirring at 20° C. After 1 hour the reaction product appeared as a precipitate and LCMS analysis revealed near complete conversion to the desired aromatic product.

The invention claimed is:

1. A continuous process for the conversion of solid carbohydrate-containing feed material into furanic compounds, the process comprising a reaction step comprising subjecting said solid feed material in a reaction medium to reaction conditions for converting said solid carbohydrate-containing feed material into furanic compounds in said reaction medium, wherein said reaction medium comprises said solid carbohydrate-containing feed material, a Brønsted acid as homogenous acid catalyst, a reactive liquid phase and an extractive liquid phase, wherein said liquid phases are immiscible with each other,
    wherein said reactor is a pulsed column reactor, and wherein the reaction medium has a reciprocating forward and backward flow during said reaction step.

2. A continuous process for the conversion of carbohydrate-containing feed material into furanic compounds, the process comprising a reaction step comprising subjecting said feed material to reaction conditions for said conversion in a reaction medium comprising a reactive liquid phase and an extractive liquid phase, wherein said liquid phases are immiscible with each other, and a Brønsted acid as catalyst,
    wherein the reaction medium comprises a solid component comprising at least a part of a carbohydrate-containing fraction of said feed material, wherein said Brønsted acid catalyst is a homogenous acid catalyst, wherein said reactor is a pulsed column reactor, and wherein the reaction medium has a reciprocating forward and backward flow during said reaction step,
    wherein said feed material comprises a polysaccharide, wherein said reaction conditions cause the opening of the solid component, hydrolysis of polysaccharides to yield monosaccharides, and dehydration of said monosaccharides in a single reaction medium, wherein the reaction conditions comprise a temperature of at least 150° C. and a pH of 2 or less, and the reaction conditions are applied to said polysaccharide in a reactor, wherein said at least two immiscible liquid phases have interfacial contact in said reactor and are in co-current flow or counter-current flow, and wherein particles comprising said polysaccharide are dispersed in at least one of said liquid phases of said reaction medium in said reactor and flow from an inlet towards an outlet of said reactor.

3. The process according to claim 2, wherein the frequency of the oscillations of the flow between forward and backward flow is 0.1 to 1.0 Hz.

4. The process according to claim 3, wherein the reactive phase is an aqueous phase and the extractive phase is an apolar organic phase, and wherein the volume ratio between the aqueous phase and the apolar organic phase is 4:1 to 1:4.

5. The process according to claim 2, wherein the feed material is heterogeneous feed material.

6. The process according to claim 5, wherein said feed material comprises one or more selected from the group consisting of
    a sieve fraction from sewage treatment comprising cellulose fibres,
    a fraction of spoiled absorbent sanitary articles comprising cellulose fibres, and
    a fraction of manure comprising cellulose fibres, and wherein the reaction medium comprises cellulose fibres.

7. A continuous process for the conversion of carbohydrate-containing feed material into furanic compounds, the process comprising a reaction step comprising subjecting said feed material to reaction conditions for said conversion in a reaction medium comprising a reactive liquid phase and an extractive liquid phase, wherein said liquid phases are immiscible with each other, and a Brønsted acid as catalyst,
    wherein the reaction medium comprises a solid component comprising at least a part of a carbohydrate-containing fraction of said feed material, wherein said Brønsted acid catalyst is a homogenous acid catalyst, wherein said reactor is a pulsed column reactor, and wherein the reaction medium has a reciprocating forward and backward flow during said reaction step, wherein said extractive phase is an organic phase comprising an alkoxyphenol.

8. A continuous process for the conversion of carbohydrate-containing feed material into furanic compounds, the process comprising a reaction step comprising subjecting said feed material to reaction conditions for said conversion in a reaction medium comprising a reactive liquid phase and an extractive liquid phase, wherein said liquid phases are immiscible with each other, and a Brønsted acid as catalyst, wherein the reaction medium comprises a solid component comprising at least a part of a carbohydrate-containing fraction of said feed material, wherein said Brønsted acid catalyst is a homogenous acid catalyst, wherein said reactor is a pulsed column reactor, and wherein the reaction medium has a reciprocating forward and backward flow during said reaction step, wherein the amount of salts provided into the reactor other than originating from the feed material is maximized to an amount corresponding to less than 1.0 M added cations in total in said reactive phase.

9. The process according to claim 1, wherein the process comprises, downstream of the reaction step wherein furanic compounds are formed, one or more downstream processing steps comprising a step wherein the formed furanic compounds are subjected to one or more chemical reactions.

10. The process according to claim 9 wherein said chemical reaction is selected from the group consisting of oxidation, reduction, hydrogenation, esterification, amidation, and a condensation reaction.

11. A continuous process for the conversion of carbohydrate-containing feed material into furanic compounds, the process comprising a reaction step comprising subjecting said feed material to reaction conditions for said conversion in a reaction medium comprising a reactive liquid phase and an extractive liquid phase, wherein said liquid phases are immiscible with each other, and a Brønsted acid as catalyst, wherein the reaction medium comprises a solid component comprising at least a part of a carbohydrate-containing fraction of said feed material, wherein the process comprises, downstream of the reaction step wherein furanic compounds are formed, one or more downstream processing steps comprising a step wherein the formed furanic compounds are subjected to one or more chemical reactions, wherein said process comprises oxidation and esterification of 5-(hydroxymethyl)-2-furaldehyde and/or furfural into a dialkyl ester of 2,5-furandicarboxylic acid, and distillation of said ester, or wherein said process comprises reacting furfural and/or 5-(hydroxymethyl)-2-furaldehyde with a hydrazine and/or hydroxylamine downstream of said reaction step.

12. The process according to claim 11, wherein said hydrazine and/or hydroxylamine is bound to a solid support, and wherein the process comprises removing said solid support from a liquid medium by solid/liquid separation together with furanic compounds bound to said solid support through a formed hydrazone and/or oxime link.

13. The process according to claim 12, wherein:
said reactor is a pulsed column reactor and the reaction medium has a reciprocating forward and backward flow during said reaction step,
a liquid stream comprising the formed furanic compounds and at least part of the organic extractive liquid phase is supplied from an outlet of said pulsed column reactor to an inlet of a downstream processing unit,
at least the hydrazine and/or hydroxylamine are added into said liquid stream in said downstream processing unit, and
the flow of the liquid stream is converted into forward only flow between said pulsed column reactor and the inlet of said unit.

14. A continuous process for the conversion of carbohydrate-containing feed material into furanic compounds, the process comprising:
a reaction step in a reactor comprising subjecting said feed material to reaction conditions for said conversion in a reaction medium comprising a first liquid phase and a second liquid phase, wherein said first liquid phase is a reactive phase and wherein said second liquid phase is an organic extractive phase, wherein said first liquid phase and said second liquid phase are immiscible with each other, wherein the reaction medium further comprises a Brønsted acid as catalyst, and a solid component, wherein said solid component comprises at least a part of a carbohydrate-containing fraction of said feed material; and
a telescoping step comprises reacting furfural and/or 5-(hydroxymethyl)-2-furaldehyde in at least part of said organic extractive second phase with a hydrazine and/or hydroxylamine in a downstream treatment unit in fluid connection with said reactor.

15. The process of claim 7, wherein said organic phase comprises 2-methoxyphenol.

* * * * *